United States Patent
Herrala et al.

(10) Patent No.: US 9,844,697 B2
(45) Date of Patent: Dec. 19, 2017

(54) METHOD AND DEVICE FOR MEASURING MUSCLE SIGNALS

(71) Applicant: FIBRUX OY, Vimpeli (FI)

(72) Inventors: Mika Herrala, Vimpeli (FI); Pasi Tavi, Kuopio (FI); Jani Mantyjarvi, Olulunsalo (FI); Mikko Vahasoyrinki, Oulu (FI)

(73) Assignee: FIBRUX OY, Vimpeli, FL (US)

( * ) Notice: Subject to any disclaimer, the term of this patent is extended or adjusted under 35 U.S.C. 154(b) by 0 days.

(21) Appl. No.: 14/397,480

(22) PCT Filed: Apr. 23, 2013

(86) PCT No.: PCT/FI2013/050452
§ 371 (c)(1),
(2) Date: Oct. 27, 2014

(87) PCT Pub. No.: WO2013/160549
PCT Pub. Date: Oct. 31, 2013

(65) Prior Publication Data
US 2015/0165269 A1    Jun. 18, 2015

(30) Foreign Application Priority Data
Apr. 27, 2012   (FI) .................................. 20125470

(51) Int. Cl.
*A61B 5/0488* (2006.01)
*A61B 5/0492* (2006.01)
(Continued)

(52) U.S. Cl.
CPC ...... *A63B 24/0062* (2013.01); *A61B 5/04014* (2013.01); *A61B 5/0488* (2013.01);
(Continued)

(58) Field of Classification Search
CPC . A61B 5/0488; A61B 5/0492; A61B 5/04004; A61B 5/0402; A61B 5/0408;
(Continued)

(56) References Cited

U.S. PATENT DOCUMENTS 4,213,466 A * 7/1980 Stulen .......................... 600/546
4,375,219 A * 3/1983 Schmid .............. A61B 5/02438
600/393

(Continued)

FOREIGN PATENT DOCUMENTS

JP          S60-158834 A       8/1985

OTHER PUBLICATIONS

Roeleveld et al. "Possible Mechanisms of Muscle Cramp from Temporal and Spatial Surface EMG Characteristics" J Appl. Physiol. 88 pp. 1698-1706 (2000).*

(Continued)

*Primary Examiner* — Linda Dvorak
*Assistant Examiner* — Erin M Cardinal
(74) *Attorney, Agent, or Firm* — Ziegler IP Law Group

(57) ABSTRACT

In order to determine the state of a muscle between a normal non-tired state, a tired state and a passive involuntary tension state, a signal from the muscle is recorded at rest by using an electrode arrangement, where an earth body may prevent the electrodes from picking up signals beyond the extent of the earth body. The frequency content of the signal is determined by spectral analysis, e.g. by computing a moment of the spectrum. A normal frequency content indicates a non-tired muscle state, whereas a low and a high frequency content indicate a tired and a passive involuntary tension muscle state. A mapping is used to improve accuracy of state determination, e.g. with a reference database.

13 Claims, 9 Drawing Sheets

(51) Int. Cl.
*A63B 24/00* (2006.01)
*A61B 5/04* (2006.01)
*A61B 5/00* (2006.01)
*A61B 5/11* (2006.01)

(52) U.S. Cl.
CPC .......... *A61B 5/0492* (2013.01); *A61B 5/4519* (2013.01); *A61B 5/0002* (2013.01); *A61B 5/1107* (2013.01); *A61B 2560/0431* (2013.01); *A61B 2562/0209* (2013.01)

(58) Field of Classification Search
CPC ............ A61B 5/04082; A61B 5/04085; A61B 5/04087; A61B 5/0416; A61B 5/0478; A61B 5/0496; A61B 5/4519; A61B 5/6801; A61B 5/6823–5/6829; A61B 5/04014; A61B 2503/10; A61B 2560/0412; A61B 2560/0468; A61B 2562/0209; A61B 2562/04; A61B 2562/182
USPC ........ 600/393, 372, 382, 384, 386–392, 546
See application file for complete search history.

(56) References Cited

U.S. PATENT DOCUMENTS

| | | | | |
|---|---|---|---|---|
| 5,111,812 | A * | 5/1992 | Swanson | A61N 1/0563 607/2 |
| 5,114,424 | A * | 5/1992 | Hagen | A61B 18/16 606/32 |
| 5,299,572 | A * | 4/1994 | Chen | A61B 5/04004 600/395 |
| 5,349,963 | A | 9/1994 | Eskelinen | |
| 6,073,039 | A * | 6/2000 | Berson | A61B 5/04085 600/372 |
| 6,522,904 | B1 * | 2/2003 | Mika | A61B 5/0492 600/374 |
| 6,597,944 | B1 * | 7/2003 | Hadas | A61B 5/0488 60/587 |
| 8,301,219 | B2 * | 10/2012 | Chen | A61B 5/04085 600/382 |
| 8,655,427 | B1 * | 2/2014 | Greenspan | A61B 5/042 600/374 |
| 2002/0026112 | A1 * | 2/2002 | Nissila et al. | 600/372 |
| 2002/0156399 | A1 * | 10/2002 | Kanderian et al. | 600/587 |
| 2003/0216663 | A1 * | 11/2003 | Jersey-Willuhn | A61B 5/0536 600/547 |
| 2004/0073104 | A1 * | 4/2004 | Brun del Re | A61B 5/0408 600/372 |
| 2004/0088036 | A1 * | 5/2004 | Gilbert | A61H 39/002 607/148 |
| 2004/0122336 | A1 * | 6/2004 | Jang | A61B 5/0531 600/547 |
| 2004/0181141 | A1 * | 9/2004 | Kislov | A61B 5/02116 600/393 |
| 2004/0254435 | A1 | 12/2004 | Mathews et al. | |
| 2005/0049517 | A1 | 3/2005 | Mathew et al. | |
| 2005/0177038 | A1 * | 8/2005 | Kolpin | A61B 5/04284 600/372 |
| 2006/0025666 | A1 | 2/2006 | Getsla et al. | |
| 2006/0094975 | A1 * | 5/2006 | Manto | 600/546 |
| 2008/0287767 | A1 * | 11/2008 | Pasveer | A61B 5/0408 600/372 |
| 2010/0198044 | A1 | 8/2010 | Gehman et al. | |
| 2011/0282179 | A1 * | 11/2011 | Zdeblick | A61N 1/05 600/393 |
| 2011/0282180 | A1 * | 11/2011 | Goldkuhl | A61B 5/0531 600/393 |
| 2013/0261423 | A1 * | 10/2013 | Herrala | A61B 5/0488 600/393 |

OTHER PUBLICATIONS

Kumar, P. et al., Spectral analysis of sEMG signals to investigate skeletal muscle fatigue, 50th IEEE Conference on Decision and Control and European Control Conference, Dec. 12, 2011, Conference Proceeding Article, pp. 47-52.

Ramathur, I. et al., Principal components of frequency domain electromyograms for muscular fatigue analysis, 32nd Annual International Conference of the IEEE EMBS, Aug. 31, 2010, Conference Proceeding Article, pp. 3519-3522.

Chattopadhyay R., et al, Towards fatigue and intensity measurement framework during continuous repetitive activities, IEEE Instrumentation and Measurement Technology Conference, Mar. 5, 2010, Conference Proceeding Article, pp. 1341-1346.

"Inter-electrode spacing of surface EMG sensors: Reduction of crosstalk contamination during voluntary contractions" De Luca Carlo J et al. Journal of Biomechanics vol. 45, No. 3, Feb. 2, 2012, ISSN: 0021-9290, DOI: 10.1016/i.jbiomech.2011.11.010, 7 pages.

Partial Supplementary European Search Report for application No./Patent No. 13781908.2-1657/2840964 PCT/FI2013/050452, dated Feb. 1, 2016, 7 pages.

Communication pursuant to Article 94(3) EPC received for European Patent Application No. EP13781908.2, dated Jul. 27, 2017, 6 pages.

* cited by examiner

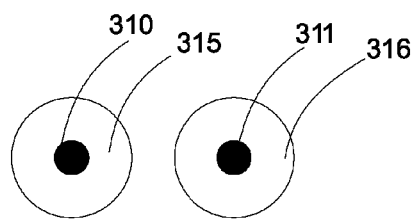
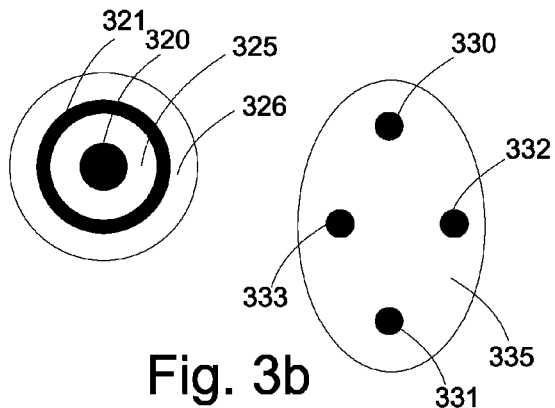
Fig. 3a
Fig. 3b
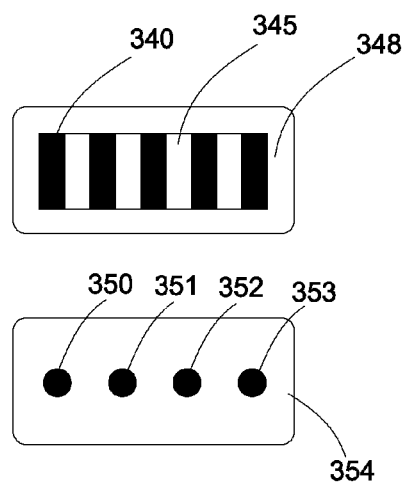
Fig. 3c
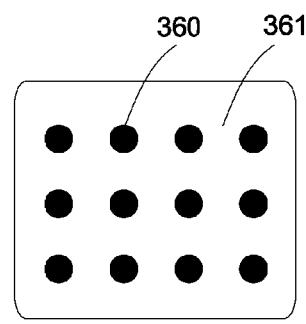
Fig. 3d
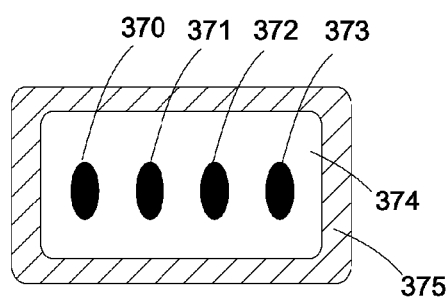
Fig. 3e
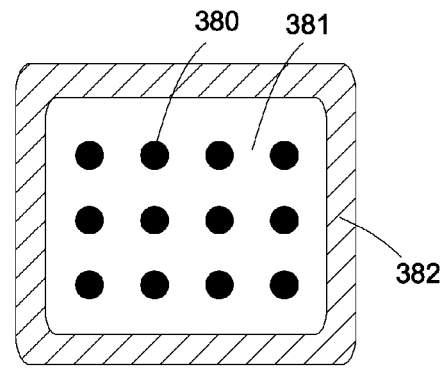
Fig. 3f

METHOD AND DEVICE FOR MEASURING MUSCLE SIGNALS

FIELD

The present disclosure relates to a method, a device, a system and a computer program product for measuring muscle signals. More specifically, the disclosure relates to the detection of the state and the properties of the muscle and a device, system and a computer program product for the same.

BRIEF DESCRIPTION OF RELATED DEVELOPMENTS

Human skeletal muscles consist of a large number of motor units that are bundles of muscle cells acting in synchrony and excited by the same neuronal signal. Skeletal muscle cell bundles, or muscle fibers may be divided into several subtypes. Type I muscle fiber (1c) is of a slow oxidative subgroup and sustains aerobic activity. Type II muscle fibers are of a fast twitch types, comprising subtypes IIa, IIb and IIx/IId) The electrical excitation of the muscle causes the muscle to contract and carry out work. The electrical excitation in the muscle can be measured as a voltage between two electrodes in the tissue or on the skin. The operation of the muscle may be analyzed from the characteristics of this signal picked up by the electrodes. The properties of the voltage signal depend on the total activity of the muscle and on the relative activity of the different types of activated motor units within the given muscle.

The strength and endurance of muscles may be developed by planned exercise. To improve performance in sports, the muscles need to be exercised so that they get tired, but so that the muscles still recover from the exercise reasonably quickly. Also, there are many contemporary professions that tend to encourage a person to stay in the same position for a long time. This also causes the muscles to get tired.

With state of the art methods and devices for analyzing the operation of muscles, it has proven to be difficult to determine when a muscle is tired to an extent that it still recovers reasonably quickly, and when the muscle is tired to an extent that recovery takes significantly longer. During a training session it is difficult to evaluate if an exercise should be continued or not, which depends of the current state of the muscles and of the characteristics of the individual in question.

There is, therefore, a need for a solution that enables a more accurate and reliable analysis of muscle signals for determining the tiredness of the muscle for example for guiding a sports exercise.

SUMMARY

Now there has been invented an improved method and technical equipment implementing the method, by which the above problems are alleviated. Various aspects of the invention include a method, an apparatus, a system and a computer readable medium comprising a computer program stored therein, which are characterized by what is stated in the independent claims. Various embodiments of the invention are disclosed in the dependent claims.

The aspects of the disclosed embodiments relate to determining the state of a muscle between a normal (non-tired, fresh) state, a tired (fatigued) state and a passive involuntary tense (PIT) state. The invention also relates to determining the properties of the muscle e.g. related to the relative proportions of different types of motor units in the given muscle. The embodiments may also be applicable to the detection of muscle properties in certain states such as myalgia, Parkinson's disease, multiple sclerosis (MS) or other demyelinating diseases. A signal from the muscle is recorded at rest (and/or during muscle activity) by using an electrode arrangement, where an earth body may prevent the electrodes from picking up signals beyond the extent of the earth body. The frequency content of the signal is determined by spectral analysis, e.g. by computing a moment of the spectrum. In a resting muscle, a normal frequency content indicates a normal non-tired muscle state, whereas a low and a high frequency content indicate a tired and a passive involuntary tension state. In other words, if the signal coming from the muscle contains an unusually high amount of high frequencies, a passive involuntary tension muscle state is determined. A tired muscle may be returned to the normal state by rest and recovery from exercise, and a passive involuntary tension state may be returned to normal state by stretching or massage. In activated muscle, the frequency content of the spectrum depends on the relative amount of different types of activated motor units. The higher is the force the muscle is producing, the higher is the frequency of the activation.

The determined high-frequency signal may be mapped using a reference function so that the mapped value may be used to determine the muscle state. For example, the mapping may produce a value that is more meaningful than a pure PIT state index, for example to a previously known muscle state indicator. Alternatively, the mapping may be used to compare the received signal's characteristics to a known population to produce a more reliable estimation of the muscle state. In the mapping, a system with a database of reference data may be used. In addition to accurate state determination, the electrode arrangement with a surrounding passive earth body that may encompass measurement electronics provides an accurate indication of the location where the signal is coming from both in depth and in horizontal position (along the skin).

According to a first aspect there is provided a method for analyzing muscle signals, the method comprising receiving a signal, the signal having been measured from a muscle in a resting state, determining a measure indicative of frequency content of the signal, determining a measure indicative of strength of the signal in a high frequency, wherein the high frequency essentially corresponds to frequencies produced by a muscle in a passive involuntary tension state, and wherein the high frequency is higher in frequency than a normal frequency, wherein the normal frequency essentially corresponds to frequencies produced by a muscle in a non-tired state, creating a mapping using the measure indicative of strength of the signal in a high frequency and a reference function, the reference function being indicative of muscle states, and determining a muscle state based on the mapping.

According to an embodiment, the method is usable for guiding an exercise using muscle signal analysis, the method comprising acquiring a signal from a muscle at rest from top of the muscle, determining a moment value of a spectrum of the signal, wherein the moment is indicative of a measure determined by multiplying a frequency value of a frequency bin with an amplitude value of the same bin to form a bin product and summing bin products for different frequencies, and wherein the moment value corresponds to frequency content of the signal, determining whether the moment has a normal value, a low value or a high value, corresponding to a normal, low and high frequency content of the signal, determining that a muscle is in a non-tired state if the moment has a normal value, determining that a muscle is in a tired state if the moment has a low value, determining that a muscle is in a passive involuntary tension state if the moment has a high value, and guiding an exercise using the determined state of the muscle. According to an embodiment, the method comprises using the mapping and the reference function to determine prediction of muscle state progression in time. According to an embodiment, the method comprises receiving a plurality of muscle signals from at least two different muscle states, and determining the measure indicative of strength of the signal in a high frequency for the plurality of muscle signals, determining muscle state estimate based on result of the mapping.

According to a second aspect there is provided a method for analyzing muscle signals, the method comprising receiving a plurality of muscle signals from at least two different muscle states, and determining measures indicative of strength of the signals in high frequency, wherein the high frequency essentially corresponds to frequencies produced by a muscle in a passive involuntary tension state, and wherein the high frequency is higher in frequency than a normal frequency, wherein the normal frequency essentially corresponds to frequencies produced by a muscle in a non-tired state, and creating at least one mapping using the measure indicative of strength of the signal in a high frequency and a reference function, the reference function being indicative of muscle states to obtain a mapping result, and determining muscle state estimate based on the mapping result.

According to an embodiment of the previous aspects, the reference function is based on a population database of muscle states, such that a number of individuals is measured to create the database, or an individual is measured a plurality of times to create the database.

According to a third aspect there is provided an electrode arrangement for use in a muscle state analyzer, the electrode arrangement comprising at least two electrodes of conducting material arranged to make contact with the skin when the electrode arrangement is operated, and an electrical insulator surrounding at least one of the at least two electrodes, the electrode arrangement characterized in that the electrode arrangement further comprises a passive earth body of a conducting material arranged to make contact with the skin when the electrode arrangement is operated, the earth body surrounding the at least two electrodes to limit the at least two electrodes from picking up a signal from outside of the extent of the earth body, the passive earth body essentially encompassing electronics to receive and handle signal from the electrode arrangement.

According to an embodiment, the electrode arrangement comprises at least two pairs of electrodes, the at least two pairs of electrodes having a different distance between the electrodes in the pair for creating a different depth sensitivity for the at least two pairs of electrodes. According to an embodiment, the at least two pairs of electrodes are arranged in either a linear arrangement essentially along one line or in a crossed setting such as the lines between electrodes in the electrode pairs forming a straight angle cross.

According to a fourth aspect there is provided the use of an electrode arrangement according to the third aspect for muscle state analysis to gather signal from the muscle in horizontal and depth dimensions.

According to a fifth aspect there is provided an apparatus for determining the state of a muscle, comprising a processor, memory including computer program code, the memory and the computer program code configured to, with the processor, cause the apparatus to receive a signal, the signal having been measured from a muscle in a resting state, determine a measure indicative of frequency content of the signal, the apparatus characterized in that it further comprises computer program code that cause the apparatus to determine a measure indicative of strength of the signal in a high frequency, wherein the high frequency essentially corresponds to frequencies produced by a muscle in a passive involuntary tension state, and wherein the high frequency is higher in frequency than a normal frequency, wherein the normal frequency essentially corresponds to frequencies produced by a muscle in a non-tired state, and create a mapping using the measure and a reference function, the reference function being indicative of muscle states, and determine a muscle state based on the mapping.

According to an embodiment, the apparatus comprises a unit for processing the signal measured from a muscle, an electrode arrangement as above and means for creating a mapping using the measure and a reference function, the reference function being indicative of muscle states, and means for determining a muscle state based on the mapping, and the apparatus is arranged to access a database as above for creating the mapping.

According to a sixth aspect there is provided a system for determining the state of a muscle, comprising an electrode arrangement, a processor, memory including computer program code, the memory and the computer program code configured to, with the processor, cause the system to acquire a signal from a muscle, determine a measure indicative of frequency content of the signal, determine a measure indicative of strength of the signal in a high frequency, wherein the high frequency essentially corresponds to frequencies produced by a muscle in a passive involuntary tension state, and wherein the high frequency is higher in frequency than a normal frequency, wherein the normal frequency essentially corresponds to frequencies produced by a muscle in a non-tired state, and create a mapping using the measure and a reference function, the reference function being indicative of muscle states, and determine a muscle state based on the mapping.

According to an embodiment, the system comprises a database for creating the mapping, the database comprising a plurality of muscle state values for creating a reference function.

According to a seventh aspect there is provided a computer program product embodied on a non-transitory computer readable medium, the computer program product comprising computer instructions that, when executed on at least one processor of a system, cause the system to receive a signal, the signal having been measured from a muscle in a resting state, determine a frequency content of the signal, determine a strength of the signal in a high frequency, wherein the high frequency essentially corresponds to frequencies produced by a muscle at rest in a passive involuntary tension state, and wherein the high frequency is higher in frequency than a normal frequency, wherein the normal frequency essentially corresponds to frequencies produced by a muscle at rest in a non-tired state, and create a mapping using the measure and a reference function, the reference function being indicative of muscle states, and determine a muscle state based on the mapping.

BRIEF DESCRIPTION OF THE DRAWINGS

In the following, various embodiments of the invention will be described in more detail with reference to the appended drawings, in which

FIGS. 3a, 3b, 3c, 3d, 3e and 3f show different electrode arrangements for measuring a muscle signal: an electrode pair, a circular and a cross electrode, two different types of linear electrodes, an electrode array, and electrode arrangements with a surrounding ground element;

DETAILED DESCRIPTION OF EXAMPLE EMBODIMENTS

Figures 1A, 1B:
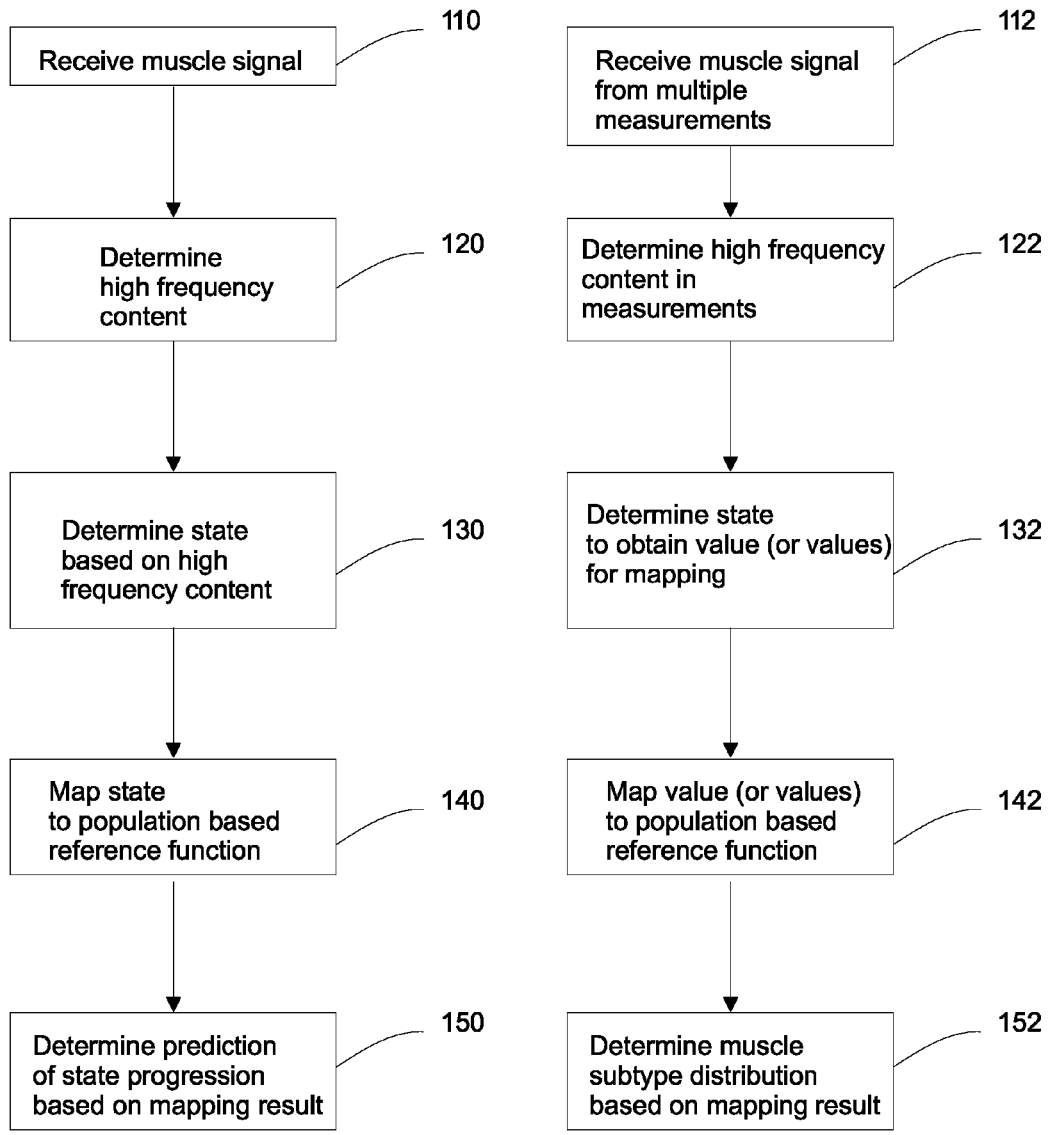
FIGS. 1a and 1b show flow charts of a method for analyzing muscle signals to determine muscle states, which may be used either to predict a muscle state progression or to determine muscle fiber subtype distribution.

In the following, several embodiments of the invention will be described in the context of a system for analyzing muscle signals to determine the tiredness of a muscle. It is to be noted, however, that the invention is not limited to this type of muscle analysis only. In fact, the different embodiments may have applications widely in any environment where recording and analysis of bioelectric signals is required.

The invention may have applications in planning and carrying out exercise of muscles for humans and animals, and it may also have applications in detecting and controlling the tiredness of muscles for any practical purpose. To this end, various devices, systems and arrangements are presented and claimed in the attached claims. These devices, systems and arrangements may have applications in private use for detecting tiredness of muscles, e.g. to help exercise a sport or to predict and/or prevent excessive tiredness of muscles for any purpose. These devices, systems and arrangements may be also used as an element in maintaining muscles in a good condition e.g. for the purposes or occupational health in a professional activity causing static tension of the muscles, and detection of jammed muscles for the purpose of physical treatment like massage, or even as tools and devices among other tools and devices aiding to diagnose and/or treat a disease related to muscles. Methods for the determination of the state of tiredness of a muscle are also presented and claimed. It is to be noted, however, that the tiredness or tension of a muscle is not a disease. Therefore, diagnostic or therapeutic methods are not a target of the present application. The different embodiments may also be used for determining the properties of the muscle e.g. related to the relative proportions of different types of motor units in the given muscle due to the different motor units producing different frequencies. The embodiments may also be applicable to the detection of muscle properties in certain states such as multiple sclerosis (MS), myalgia or Parkinson's disease, since the frequencies produced by muscles in these states may be different. It is to be noted, however, that diagnostic methods are not a target of the present application, since the detected muscle properties merely offer information on the muscle state, and if a diagnosis of a disease is being made by a doctor, the muscle state information may be only one technical parameter to be considered. A device according to an embodiment will not carry out any diagnostic method or offer a diagnostic result.

A muscle consists of motor units, as explained earlier. These motor units may be individually innervated so that an order to contract may be delivered individually to the motor units. Some of the motor units, e.g. the smaller and slower ones, may be more easily activated than other motor units. Each type of motor unit has its characteristic frequency range produced by the electrical activity of the motor unit. The activity of the slow, fatigue resistant muscles is at lower frequency than the activity of the fast, easily fatigued muscles. Depending on the type of work and the condition of the muscle, different motor units may be activated. The electrical activation of the muscle cells causes them to contract, and they carry out work. Furthermore, also in the resting state of the muscle, some motor units are sporadically activated and such a pattern of activation causes a so-called resting tonus of the muscle. In other words, even a resting muscle is not completely passive, but has a small amount of constant activity happening. The contraction and the stable length of the muscle is in part controlled and maintained by so-called muscle spindles that are units that sense the elongation and pressure in a muscle and are able to act as feedback units in the muscle-nerve system. Muscle spindles may also cause contraction of the muscle cells. Underlying the mechanical activation of the muscle is an electrical excitation taking place in the muscle cells.

The propagation of the electrical excitation of a muscle creates a varying electric potential that is measurable from the body surface by means of electrodes and a voltage measurement device suitable for measuring such signals. Such a signal may be called an electromyogram (EMG). The EMG signals from a resting muscle picked up from the body surface between two electrodes may be of the order of some microvolts or tens of microvolts, e.g. 5-20 µV, by their amplitude. The rest EMG signals contain also smaller fluctuations of the order of 1 µV or less. From a working and moving muscle, the EMG signals may be significantly larger.

The voluntary movements of skeletal muscles are controlled by a motor cortex of the brain. Each motor unit of a muscle is controlled by a given sector of the motor cortex. A neural impulse sent to a motor unit from the motor cortex carries a frequency and this impulse frequency is proportional to the force required from the muscle. An activation frequency reflects a level of frequency required to activate a certain motor unit. A low motor cortex activation frequency activates in each muscle only the lowest impulse frequency requiring motor units, whereas higher motor cortex frequency activates motor units requiring higher frequency. This phenomenon can be called the recruitment order. The recruitment order impulse system could, for example, be depicted as a selectoroperating based on the modulation frequency, which determines the motor units to be activated at a given moment.

Due to the different activation frequency levels between low frequency level motor units and high frequency level motor units, an EMG signal frequency correlates at least approximately proportionally with the muscle activity and exercised force.

The motor units have different sizes in terms of length and thickness. The electrical excitation in a muscle cell bundle may have a different propagation speed and frequency range produced by the activation depending on the thickness (diameter) of the bundle—e.g. the thicker the bundler, the faster the propagation speed. Furthermore, the rate of rise of the excitation of the muscle bundle, i.e. the rate of change in the voltage across the cell membranes in the bundle, may vary according to the diameter of the bundle and/or the rate of rise of the excitation. The voltage signal picked up by the electrodes may therefore be different depending on which muscle cell bundles are excited. If fast muscle cell bundles with a large diameter are excited together with slower and smaller muscle cell bundles, such as in a non-tired normal muscle, the frequency content of the signal picked up by the electrodes contains a normal, wide frequency distribution. According to existing knowledge, it is known that when a muscle is exercised and it gets tired the signal at rest consists predominantly of lower frequencies. This may be due to the fast muscle cell bundles with higher frequency activity getting tired more rapidly.

The frequency content of an EMG signal from a muscle may be analyzed with high precision and accuracy with embodiments of the present invention. This frequency content analysis enables the identification of activation frequency ratio of different motor units in a muscle. This frequency ratio correlates with the ratio of fast and slow motor units in a muscle. As different motor units represent different muscle fiber subtypes with different properties, the EMG signal frequency content has been noticed here to correlate with the muscle activity and exercised force. Further, certain alterations which lead to a muscle behaving in a different manner, such as changes observed in muscle properties in certain states such as multiple sclerosis (MS), myalgia or Parkinson's disease, have been noticed to correlate with the electromyogram signal frequency. For example, in demyelination disorder the conductivity of fast motor units is considerably attenuated, which restricts the neuronal impulse frequency in these motor units.

In the invention, it has been realized that the status a muscle that is not only mildly tired but in passive involuntary tension may be detected by determining the high frequency content of the signal that the muscle creates at rest. This is in contrary to what is commonly understood of muscle signal analysis. In the invention, a method and devices have been created where the muscle signal is acquired with the help of electrodes, and a deviation in the frequency content of the signal towards the higher frequencies is used as an indicator for a passive involuntary tension state of the muscle. The degree of tiredness may also be detected by comparing the frequency content at the low frequencies, at the normal frequencies and at the high frequencies. Furthermore, spectral analysis may also be used to estimate the endogenous properties and motor unit composition of the muscle due to the different frequencies these motor units produce. This may comprise measurements from both active and resting muscle. The different devices that may employ the invention comprise, without limiting to these examples, at least a hand-held or movable muscle analyzer, a portable exercise computer, a wireless sensor attached to or implantable into the body, a physiological monitoring system for pilots embodied in a suit, an intelligent garment, a chair or another piece of furniture, and a treatment bed e.g. to be used in giving massage.

FIGS. 1a and 1b show flow charts of methods for analyzing muscle signals to determine muscle states, which may be used either to predict a muscle state progression or to determine muscle fiber subtype distribution. In FIG. 1a, in step 110, a signal measured from a muscle is received. The signal may have been measured e.g. with the help of electrodes or sensors sensing the magnetic field, or otherwise in a way that the signal is indicative of the electrical activity in the muscle. The signal may then be converted to digital format e.g. by analog-to-digital conversion, or the signal may be directly acquired in digital format. The signal is then e.g. stored in a memory, transmitted along an electric, optical or wireless connection or otherwise brought to be accessible for analysis.

At phase 120, the frequency content of the muscle signal is determined. The frequency content may be determined e.g. by performing a transform such as a Fourier transform, a fast Fourier transform, a discrete cosine transform, a wavelet transform or any other suitable transform. The transform may be used to convert the signal from time domain to frequency domain. Alternatively, the conversion may be omitted, and coefficients and results of the whole or partial transform may be used as input to a method for determining a high frequency content of the signal. The frequency information of the signal may be further processed e.g. by determining the energy and/or amplitude at different frequency bands such as 8-30 Hz (low frequency band), 20-60 Hz (normal frequency band) and 50-150 Hz (high frequency band). For some applications, the low-frequency band may start from as low as 0.5 Hz or lower and end as high as 40-50 Hz or higher. The middle band may start from 30-40 Hz and end at 50-80 Hz. The high-frequency band may start from 40-70 Hz and end at 100 Hz, 200 Hz, 300 Hz or higher. The bands may overlap, or there may be gaps between the bands. Alternatively, or in addition, the frequency content may be characterized by computing a number associated with different moments of the signal, as explained in the context of FIG. 2. A high moment number may be indicative of a frequency content at higher frequencies. The signal may also be analysed in time-domain, e.g. by zero-crossing analysis or by measuring peak-to-peak times from the signal (the smaller the time, the higher the frequency) For any of the analysis methods, the signal may be pre-processed before analysis, for example filtered and/or the signal may be scaled and/or normalized or the analysis results may be scaled and/or normalized. The signal may be processed so that higher and lower frequencies change place or are otherwise altered. The detection of characteristics of the original signal relating to the normal, tired and passive involuntary tension state may take place from such a processed signal.

At phase 130, the detected frequency content is used to determine the state of the muscle. If frequencies at a middle area are detected, or the frequency distribution resembles that of a signal from a non-tired normal muscle at rest, the muscle may be determined to be in the non-tired state. If low frequencies are detected, the muscle may be determined to be in the mildly tired state. If high frequencies compared to the non-tired muscle are detected, the muscle may be determined to be in a passive unvoluntary tension state. The result of the determination may then be indicated to a user. It may also be feasible to indicate the level of tiredness to a user. Alternatively or in addition, a threshold may be set beyond which a passive involuntary tension state of the muscle is indicated.

At phase 140, the measured state determined at the previous phase 130 is mapped to a reference function, which may be called a decision surface. The decision surface may be based on a population database of muscle states and therefore indicative of said muscle states. The database may be for example a population based database, such that it comprises measures of muscle states of a number of individuals. Alternatively, or in addition, an individual may be measured a plurality of times to create the database. According to an embodiment of the invention the measures that may be stored into a database, such as values derived from gathered signals, may also originate from a given motor unit or motor units in a given muscle and vary in horizontal and depth dimensions. This allows the creation of a multi-dimensional database, which may function as a decision surface. This decision surface may comprise information of the measures, such as location information of horizontal or depth dimension of the measures, index information of normal (non-tired, fresh) state, a tired (fatigued) state and a passive involuntary tense (PIT) state or information of exercised force (load) used in measures. By creating a such decision surface based on reference data, a measure may be mapped (fitted) into the decision surface to determine the muscle state. The use of mapping to a reference function or decision surface may increase the reliability of the muscle state determination.

Further, if the database comprises information gathered of a population comprising normal (healthy) muscles and of muscles with various muscle or neuronal disorders, a non-limiting exemplary listing comprising states such as myalgia, Parkinson's disease, multiple sclerosis (MS) or other demyelinating diseases, a muscle state from a person may be determined by mapping an obtained measure into a decision surface or a reference function comprising said information. In other words, when reference data is available for a comparison, mapping may be used to indicate a muscle state.

At phase 150, the result of the mapping may be used to determine a prediction of the progression of the muscle state. In predicting a progression of a muscle stage, such as fresh, fatigue of PIT, multiple measures may be used to increase the sensitivity of the prediction and slope of the progression. Further, the decision surface may be used to show the horizontal location and depth of the muscle, which may be used for example to optimize a training session or to determine problems or pains during an exercise or due to an altered muscle state. The decision surface mapping may further be used to locate neuromuscular problems, as the depth location of data signal may identify the muscle, and the horizontal (along the skin surface) information may identify the place of a neuromuscular junction. In a training exercise a person may have instantaneous information available in which to adapt his exercise load and repeats.

The mapping and prediction of muscle state progression is of importance, as earlier, at phase 130, only a static value is indicated. While the static value is accurate, the physiological parameters in a given individual may cause a source of variation, which the decision surface is able to diminish by mapping the value to a larger reference set with thresholds. Therefore, by creating a mapping and using a measure indicative of strength of a signal in a high frequency and a decision surface, a muscle state may be determined with higher reliability and sensitivity.

In FIG. 1b, at phase 112, a plurality of muscle signals are received and measured. The measures are indicative of strength of said signals in a high frequency. There may be two measurements, or more than two measurements. The signals are measured in at least two different muscle states. A 'different muscle state' in this may refer to, for example a first muscle state and a second muscle state that differ in time, and during which electrical activity has occurred in the muscle. For example, if a muscle is first in a resting state and is then exercised, it confers to said definition of a different muscle state for said muscle. Similarly, if said muscle is after exercise returned into a resting state, it is in a different muscle state. Different muscles may be in a different state also, for example if the muscle fibre subtype distribution is different between said muscle fibers. Different muscles may be in a different state also, for example due to an alteration which leads to a muscle behaving in a different manner, such as changes observed in muscle properties in certain states such as multiple sclerosis (MS), myalgia or Parkinson's disease.

At phase 122, the frequency contents of the muscle signals are determined as described in FIG. 1a phase 120. At phase 132 the determined frequency contents from at least two different muscle states, are used to determine muscle states, which are measures indicative of strength of the signals in high frequency, wherein the high frequency essentially corresponds to frequencies produced by a muscle in a passive involuntary tension state, and wherein the high frequency is higher in frequency than a normal frequency, wherein the normal frequency essentially corresponds to frequencies produced by a muscle in a non-tired state. These states are used to create values, such as a first muscle state value and a second muscle state value, said values corresponding to said muscle states, which values may be used for mapping based on a reference function or a decision surface. When creating at least one mapping using the measure indicative of strength of the signal in a high frequency and a reference function, the reference function being indicative of muscle states to obtain a mapping result, as shown in phase 142 a muscle state estimate based on the mapping result may be determined, as shown in phase 152. According to an embodiment, when information of two different muscle states is compared against a reference function in the mapping, a dependent function may be formed. This dependency may be determined as an estimate, when the mapping result correlates with a reference function based on a population data from a database. The estimate may be, for example a muscle subtype distribution. The distribution of various muscle subtypes is informative, and has many applications. Various exercises require a predominance of certain muscle fiber type utilization over another. For example, aerobic events, use a higher percentage of Type I (slow-twitch) muscle fibers, whereas anaerobic events uses predominantly Type II (fast-twitch) muscle fibers. By defining the progress of a muscle state during an exercise and producing information of the muscle fiber subtype distribution and changes in these, a person, or an animal, may be evaluated and analyzed for suitability to a given sport type. According to an embodiment, for example, a person with a muscle fibre subtype distribution consisting mainly of Type I (slow-twitch) fibers could be predicted to perform better in aerobic events. Furthermore, according to an embodiment of the invention, the method may be used to manufacture a device which may indicate a progressive change in a muscle fiber type distribution. Such a device could be used to help detect early changes of muscle properties in certain states such as multiple sclerosis (MS), myalgia or Parkinson's disease, or to follow up the development due to training.

Figure 2:
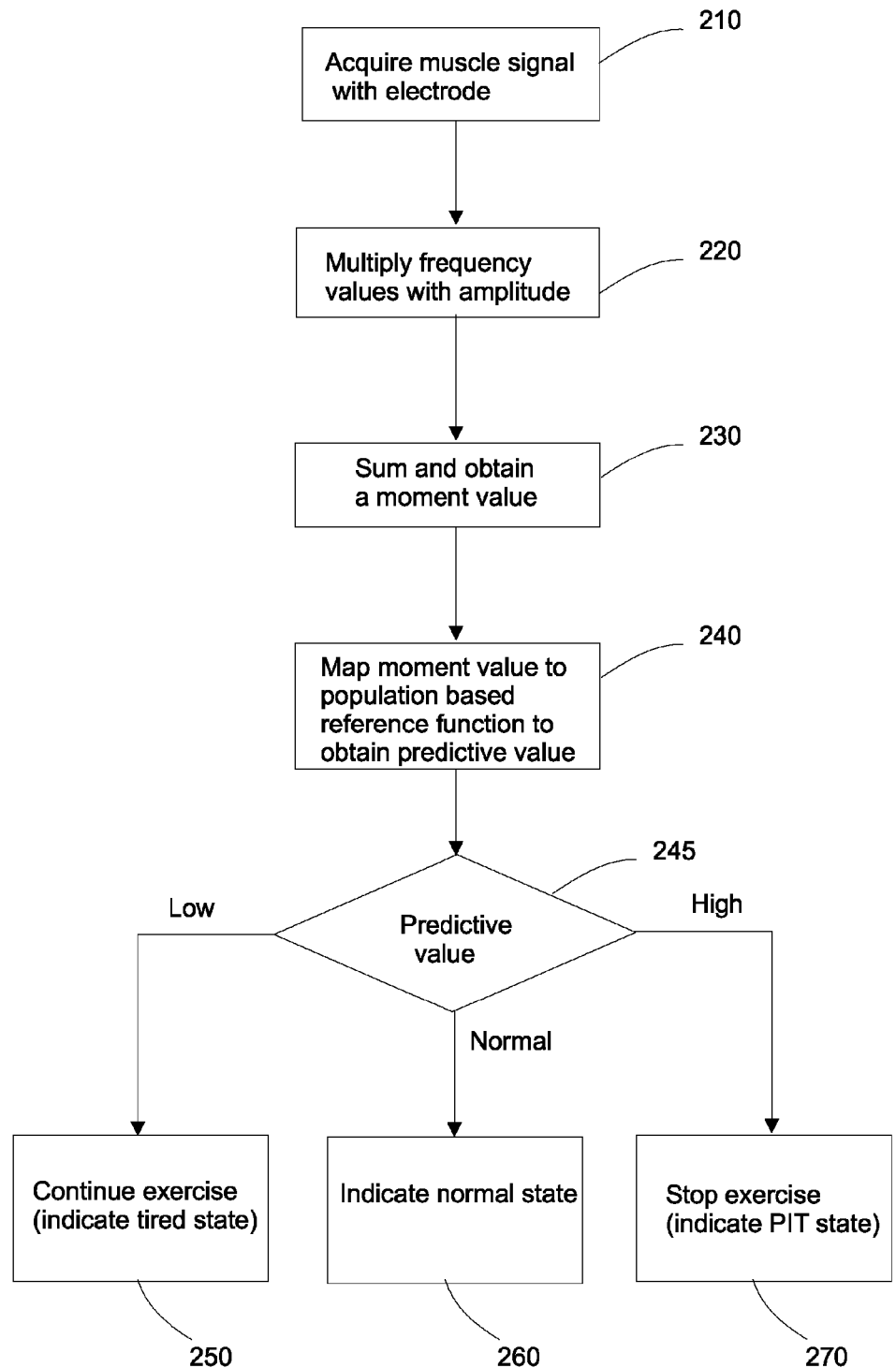
FIG. 2 shows a flow chart of a method for determining the spectral content of a muscle signal.
Figure 6A:
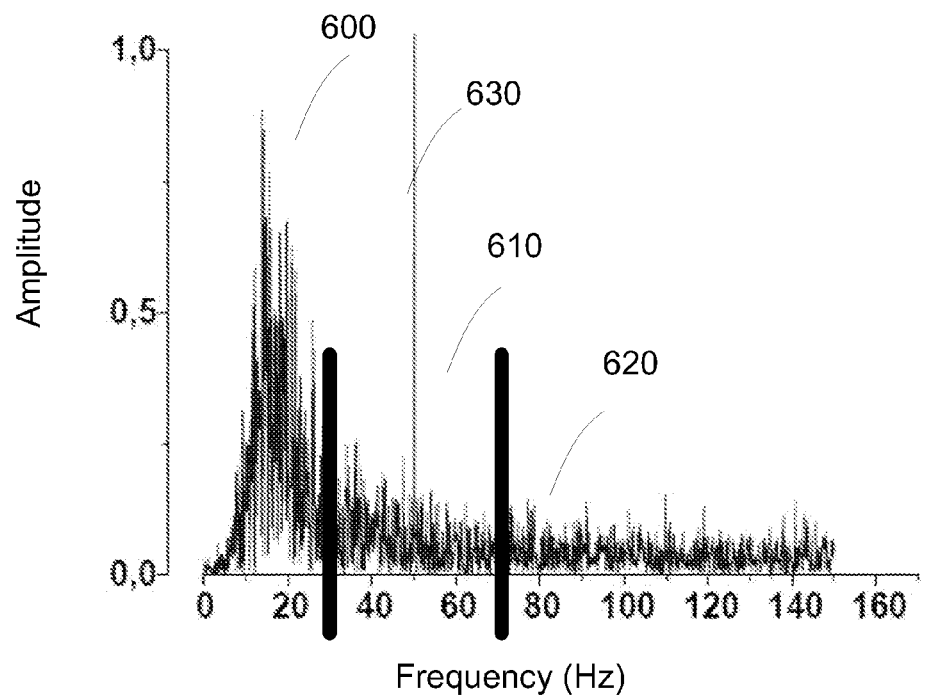
FIG. 6a shows a spectrum of a signal from a muscle in a non-tired normal state.

FIG. 2 shows a flow chart of a method for determining the spectral content of a muscle signal. In step 210, the signal from the muscle may be acquired e.g. with an electrode setup such as shown in FIGS. 3a to 3f. As explained earlier, the signal is converted to digital format for analysis. The signal may then be analyzed e.g. by Fourier transform, as also explained earlier. This may result in a spectrum such as shown in FIG. 6a, where amplitude (a) values according to frequency (f) are shown.

In step 220, the frequency values f may be multiplied with amplitude values a or otherwise combined. This may happen so that the frequency and amplitude values are formed into vectors so that the vector f comprises elements $(f_1, f_2 \ldots, f_n)$ where n is the number of spectral bins and the vector a comprises elements $(a_1, a_2 \ldots, a_n)$. The corresponding elements in the vectors are then multiplied, and summed together in step 230 to obtain a moment value or a spectral sum ss as an inner product of the vectors f and a according to formula ss=f·a. In the case presented above, the spectral sum is the first moment of the signal spectrum, and describes the location of the center of weight along the frequency axis. In other words, if the signal contains low frequencies, the spectral sum or the first moment have a small value, and if the signal contains high frequencies, they have a large value.

In step 240, the moment value or the spectral sum is evaluated e.g. against thresholds or by some other decision making method. Advantageously the moment value is mapped to a reference function, such as a population based function described earlier in FIG. 1. The mapped moment value may be used to obtain a predictive value, to be used in step 245. If the signal is determined to have low frequencies (the spectral sum is small) compared to a signal from a normal non-tired muscle, a slightly tired muscle state is indicated in step 250. By using the mapping with the reference function, this state can be predicted as 'normal' tired stage, and may be used, for example, to announce that an exercise may be continued. If the signal is determined to have medium frequencies (the spectral sum is of medium value), a non-tired muscle state is indicated in step 260. If the signal is determined to contain more high frequencies than a signal a normal non-tired muscle (high value of the spectral sum), a passive involuntary tension state of the muscle is indicated in step 270. Again, by using the mapping with the reference function, this state can be predicted as PIT stage, and may be used, for example, to announce that an exercise should be discontinued.

FIGS. 3a, 3b, 3c, 3d, 3e and 3f show different electrode arrangements for measuring a muscle signal. In FIG. 3a, an electrode pair is shown. The electrode pair may be a fixed pair so that the distance between electrodes 310 and 311 stays the same when the electrode pair is applied to the skin, or it may consist of two separate electrodes. The electrodes may be surrounded by electrical insulators 315 and 316 such as plastic, glass, porcelain, or air. In the case of air, the electrode may be essentially without any solid state insulator. The electrodes may be pieces of conducting material such as metal, semiconductor, carbon, conducting plastic or a composite material such as silver/silver-chloride mixture. The electrodes may be circular, rectangular, symmetric or asymmetric, or round or elongated in shape. The insulators 315 and 316 may be common to both electrodes, i.e. be physically the same object or two objects connected to each other, or they may be separate. What has been said about the materials and setup of the electrodes in case of an electrode pair may apply mutatis mutandis to other setups illustrated in FIGS. 3b to 3e. The shape of the lead field of an electrode pair such as in FIG. 3a is such that the electrode pair essentially picks a signal from the muscle at the same depth as the distance between the electrodes 310 and 311. The sensitivity of an electrode pair may therefore be tuned to different depths by altering the distance between the electrodes.

FIG. 3b displays two planar electrode setups. The electrodes 320 and 321 are concentric and pick up essentially a so-called Laplacian signal, i.e. a derivative signal of the one picked up by an electrode pair. The Laplacian electrode may be sensitive to signal sources below the electrode. Again, the electrodes may be separated and/or surrounded by insulators 325 and 326. In another setup, there are four electrodes 330, 331, 332 and 333 making up e.g. two electrode pairs in a cross-form setting. The electrodes 330 and 331 may be spaced apart by a different distance than the electrodes 332 and 333. Again, the electrodes may be surrounded by an insulator 335.

FIG. 3c displays two linear electrode setups. The electrodes 340 are arranged in a row with an insulator 345 between each two electrodes. There may be any number of electrodes, such as 3, 5, 7, or 10, or even a very high number like 50 or 100 in the linear strip of electrodes. The linear electrode arrangement may be surrounded by an insulator 348, where the insulator 348 may be of the same material as and in connection with the insulator 345, or it may be different material. The electrodes 350, 351, 352 and 353 are also arranged along a line, and they may be surrounded by a common insulator 35.

FIG. 3d displays an array of electrodes. The electrodes 360 may be arranged in a regular or irregular shape, for example in a grid of N by M electrodes, or electrodes being distributed randomly, or in a hexagonal setting. The electrodes may be surrounded by a common insulator 361.

FIG. 3e displays a linear electrode arrangement surrounded by a ground body or element. The electrodes 370, 371, 372 and 373 may be arranged linearly, and they may be elongated in shape such that the elongation of the electrodes is perpendicular to the line along which the electrodes are arranged. The electrodes may be surrounded by an insulator 374. In the setup of FIG. 3e, there is a ground body or ground element 375 at least partially or completely surrounding the setup. The term surrounding may be understood loosely so that the ground body merely extends away from the set of electrodes, and is, for example, placed on at least two opposite sides of the electrodes. The ground body may not be an active member in the signal acquisition, and the ground body may be merely a large conducting object without any active elements or without being connected to the acquisition electronics in any way. The ground body may also extend in the depth dimension so that it forms a box open from one side around the electrodes (the box may have a passage for the electrode wires). The ground body may work to restrict the lead field of the electrode arrangement so that it even more precisely picks up signals below the arrangement and is insensitive to signals coming from the side. In addition, the ground element may protect the electrodes from picking up ambient electromagnetic noise. The ground element may also surround any other electrode setup such as the electrode array, as shown in FIG. 3f, where the electrodes 380 are surrounded by an insulator 381 and a ground element 382.

Figure 4A:
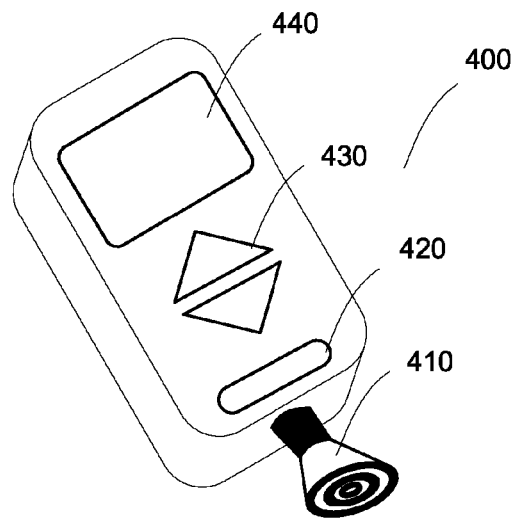
FIGS. 4a, 4b and 4c show a hand-held muscle signal analyzer and electrode heads for the same.

FIG. 4a shows a hand-held muscle signal analyzer 400. The apparatus has an electrode head 410 that may be attached and disconnected from the apparatus as needed. This arrangement enables the electrode arrangement to be changed as needed, for example by type of muscle to be analyzed. Electrode arrangements with deeper sensitivities may be used with deeper and/or larger muscles, and there may be electrode heads suitable for even and uneven or curving skin surfaces. The different electrode heads may have different material. Further, the electrode heads may be personal or they may be single-use to improve hygienity. The apparatus may also comprise buttons for controlling the operations, for example an acquisition button 420 and user interface control buttons 430. There may be a display or a led indicator 440, or a speaker for emitting a sound for the purpose of showing to the user the result of the muscle state analysis.

Figure 4C:
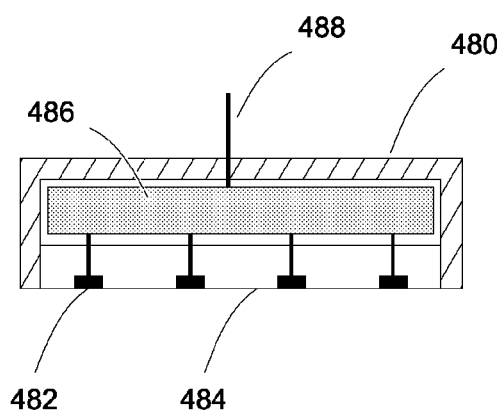
Figure 4B:
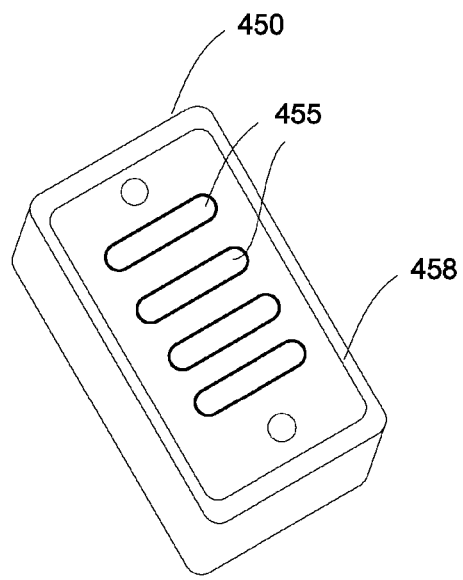
Figure 4B:
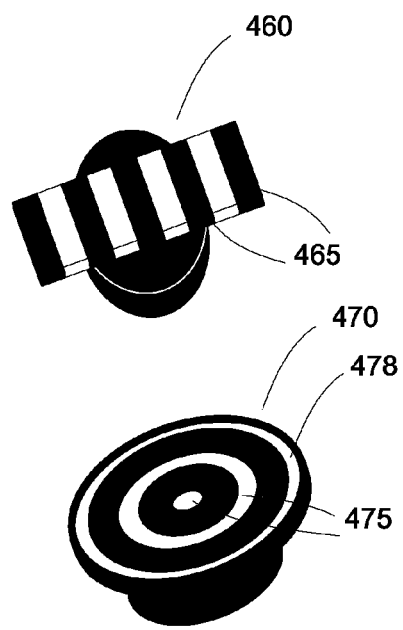

FIG. 4*b* shows electrode heads for a hand-held muscle signal analyzer. The electrode head 450 is of a linear type where the electrodes 455 are arranged in a linear manner. The electrodes 455 may be elongated in shape, and to improve contact, they may be slightly elevated above the insulating material surrounding them. The casing 458 of the electrode head 450 acts as a grounding body and it makes contact with the skin, as well. The electrode head 460 is a different type of a linear electrode with the electrodes 465 being separated by insulating elements. The electrode head 470 is of the circular type where the electrodes 475 are concentric. The electrode head has a grounding body 478. All of the electrode heads have a connector for physically and/or electrically connecting the head to the analyzer. The electrode heads may be passive, or they may be active so that they contain acquisition electronics for amplifying and/or digitizing the signal picked up by the electrodes.

FIG. 4*c*. shows a cross section of a hand-held muscle signal analyzer. The electrodes 482 are arranged in a linear manner, and the insulating material 484 surrounds them. The casing 480 acts as a passive earth body and essentially encompasses electronics 486 to receive and handle signals from the electrode arrangement. In other words, the passive earth body is arranged to make electrically conductive contact with the skin from one or more sides of the electrode arrangement. The earth body may also extend to cover the top of the electrode arrangement, and may essentially leave an opening or recess to which the electrodes and the electronics may be installed. A lead-in 488 may be provided for wired, optical or wireless connection for transferring signals, commands and data from the device. When the electronics are located inside a passive earth body, they are shielded from external electrical disturbances and the signal quality and transmission sensitivity may be significantly improved. The passive earth body may cause the electrode setup to be insensitive to signals coming from the side and in addition protects the electrodes and electronics from picking up ambient electromagnetic noise that may e.g. be coupled to the human body being measured and picked up in a conventional, prior art electrode setting. According to an embodiment, for example an analogue-to-digital transformer and a signal amplifier may be located inside the passive earth body, which would allow a digital signal to be transmitted from the electrode unit to an acquisition unit.

Figure 5A:
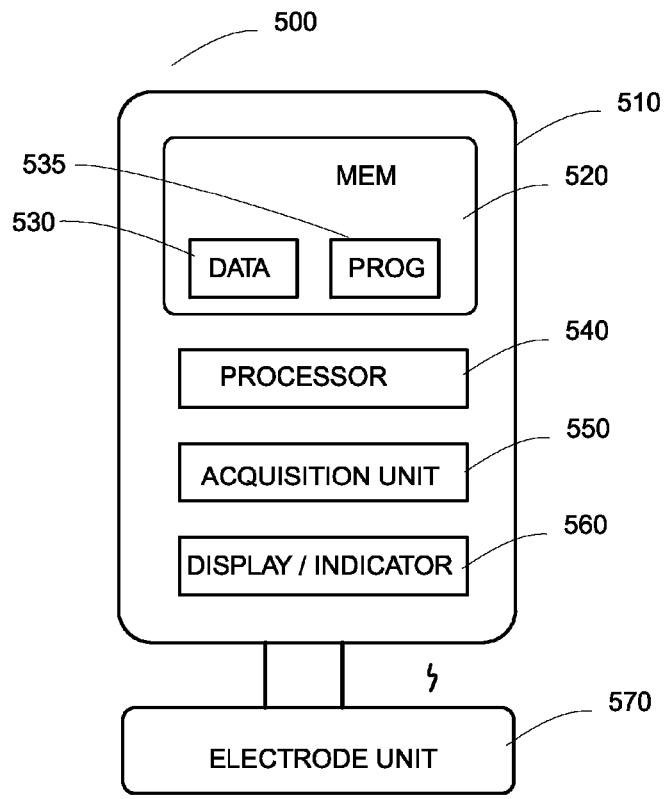
FIG. 5a shows a block diagram of an apparatus for determining the state of a muscle.

FIG. 5*a* shows a block diagram of an apparatus 500 for determining the state of a muscle. The apparatus may be embodied in a casing 510 suitable for holding the apparatus by hand for carrying out the acquisition of the muscle signals. The apparatus may have a processor 540, memory 520 for holding data 530 such as the acquired signal and programs 535 such as the frequency content analysis program and/or the acquisition control program and/or the user interface program. The apparatus may have an acquisition unit 550 for amplifying and/or digitizing the signal picked up by the electrode unit 570. The functionality of the acquisition unit may also be partly or completely implemented in the electrode unit. There may also be a display or indicator unit 560 for showing or indicating the result of the analysis to a user. The apparatus may function so that the acquisition and indication is done in a one-shot manner, or so that the acquisition, analysis and indication happens continuously, thereby allowing the apparatus to be moved along the skin to detect the areas in the muscles that are in the passive involuntary tension state. The apparatus may indicate the passive involuntary tension state by a sound or a light signal. The connection between the apparatus and the electrode unit may be wired, optical or wireless. According to an embodiment, the electrode unit may comprise a transmitter with a wireless connection.

Figure 5B:
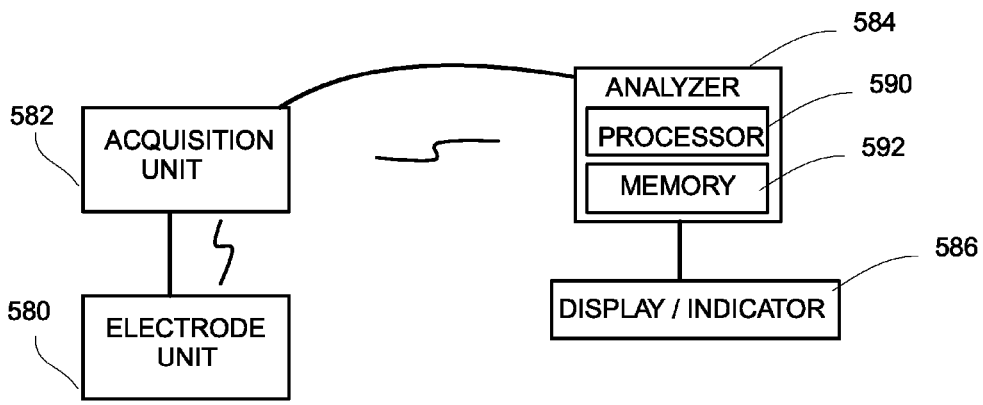
FIG. 5b shows a block diagram of a system for determining the state of a muscle.

FIG. 5*b* shows a block diagram of a system for determining the state of a muscle. The system may have an electrode unit 580, an acquisition unit 582, an analysis unit 584 comprising a processor 590 and memory 592, and a display/indicator unit 586. The various units may have various degree of functionality, e.g. they may contain circuitry, processors, memory and communication means in addition to their basic functionality. The different units may be implemented as separate devices, or some or all of them may be combined in the same device. In addition, the different units and devices may be connected to each other via a wired, optical or wireless connection for transferring signals, commands and data.

Figure 5C:
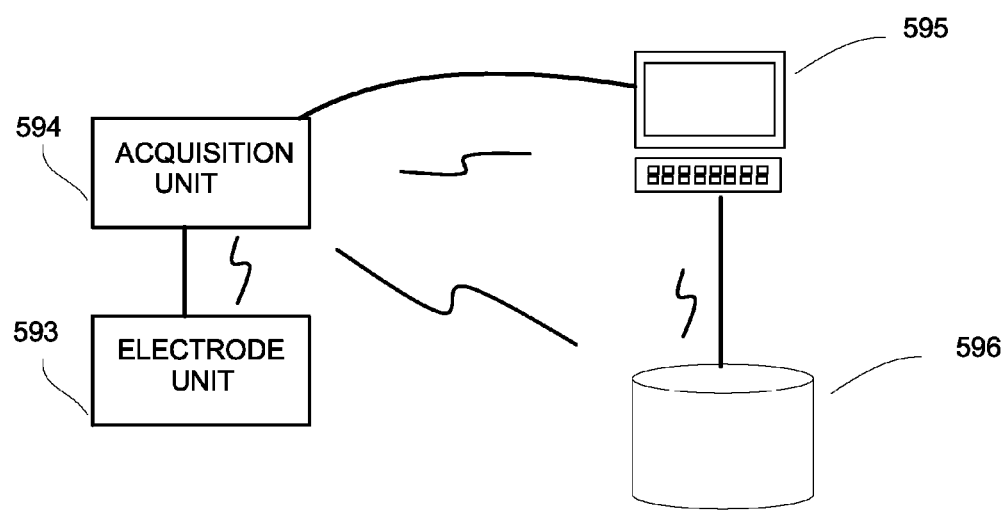
FIG. 5c shows another block diagram of a system for determining the state of a muscle.

FIG. 5*c* shows another block diagram of a system for determining the state of a muscle. The system may have an electrode unit 593, an acquisition unit 594, an analysis unit 595 comprising a processor and memory, such as a computer, and a server 596. The various units may have various degree of functionality, e.g. they may contain circuitry, processors, memory and communication means in addition to their basic functionality. The different units may be implemented as separate devices, or some or all of them may be combined in the same device. In addition, the different units and devices may be connected to each other via a wired, optical or wireless connection for transferring signals, commands and data. According to an embodiment the electrode unit 593 may communicate with the acquisition unit 594. The acquisition unit may be connected to the analysis unit 595, which may be connected to the server 596. Alternatively, the acquisition unit may be connected directly to the server 596. The server may contain a database, which can be used to create a reference function for mapping purposes. The database may comprise a plurality of muscle state values and may be used for creating a reference function. The database on the server 596 may operate as a remote service, where the measures are sent for mapping. Alternatively, or in addition, the database may function on a data transmission mode, in which case a reference function is first downloaded to the analysis unit 595 or acquisition unit 594, where the acquired muscle state data may be processed and the measures mapped against a reference function, which is indicative of muscle states. By either of these means, the mapping may be used to determine a muscle state and predict a progression of the muscle state. By arranging the access to the database these means may be used to create the mappings, which further may be used to determine muscle fibre subtype distributions. The server with a database enables an improved use of the system, as the acquisition unit or the analysis unit may not have to comprise all the data for the reference function locally. Instead, the data may be retrieved trough a server connection, which provides an efficient and rapid method for the mapping. Further, the use of a server with a database for mapping practically eliminates the need to calibrate the system for user defined parameters, as the reference function (or functions) provides information which may be used to determine thresholds for different muscle states or state progression predictions. According to an embodiment, the use of the server with a database may further be used to selectively download a decision surface comprising a reference function set required in a given measurement, for example a reference function set based on a training program, which comprises selected data of performed exercised during a defined training period. According to an embodiment, the data structure may be purchased or selected form an internet service and the data structure may then influence or control the operation of the muscle signal acquisition unit or analysis unit.

FIG. 6a shows an example spectrum of a signal from a muscle in a non-tired normal state. The spectrum shows relatively high content of low frequencies 600 in the signal, and a clear content of medium frequencies 610. The high frequencies 620 are clearly lower in the signal acquired from a normal non-tired muscle at rest. The spectrum also shows the 50 Hz ambient electrical noise 630 picked up by the acquisition unit.

Figure 6B:
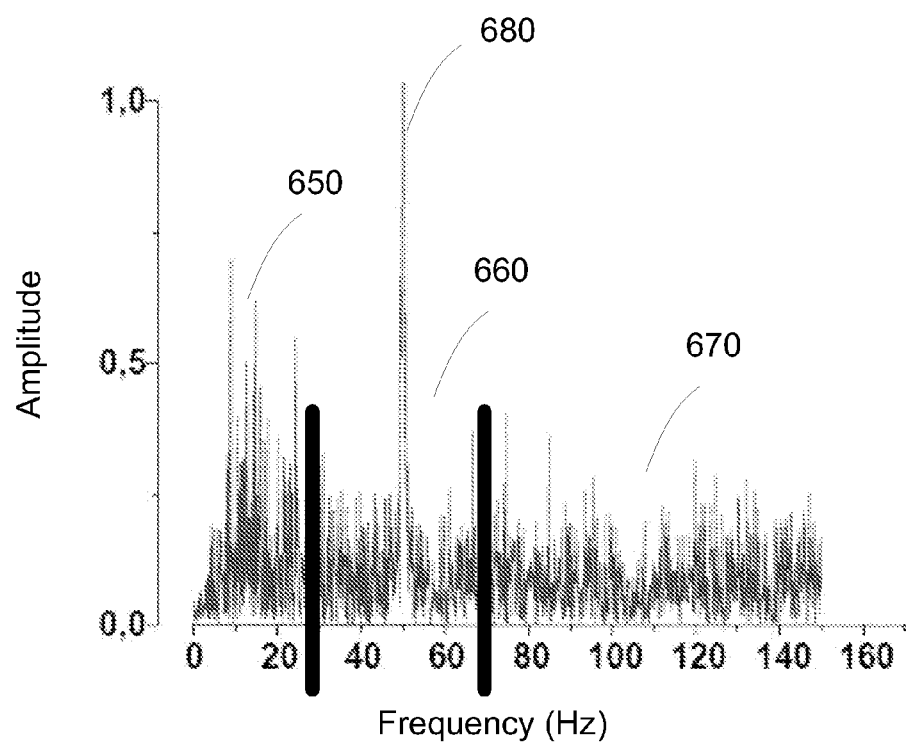
FIG. 6b shows a spectrum of a signal from a passive involuntary tension muscle.

FIG. 6b shows an example spectrum of a signal from a passive involuntary tension muscle. Compared to the spectrum of FIG. 6a, the low frequency content 650 of the signal from a passive involuntary tension muscle is lower than for a non-tired muscle. This is contrary to what is conventionally understood of the behavior of muscle signals. The medium frequency content 660 of the signal from a passive involuntary tension muscle shows some increase compared to a non-tired muscle. There is a clear increase in the high frequency content 670 of the signal from a passive involuntary tension muscle compared to a non-tired muscle. Correspondingly, the normalized spectral sum indicator for the passive involuntary tension muscle is higher compared to the non-tired muscle. The ambient 50 Hz noise 680 is again present.

Figure 6C:
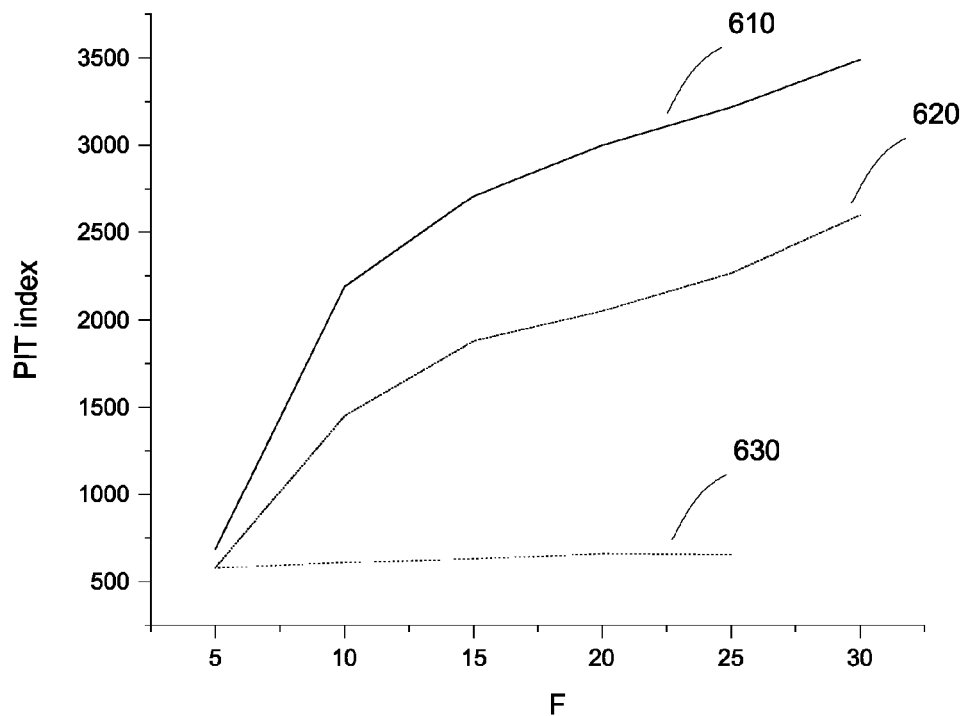
FIG. 6c shows a diagram of reference function for mapping to determine prediction of muscle state progression or to determine muscle fibre subtype distribution.

FIG. 6c shows a diagram of reference function for mapping to determine prediction of muscle state progression or to determine muscle fibre subtype distribution. The horizontal axis represents the incremental force (in newtons) and the vertical axis represents the activation frequency (in PIT state index values). Different reference functions 610, 620, 630 may be created, where measures indicative of strength of signals in a high frequency from muscles may be mapped. The reference function 610 represents a fast muscle, where a motor unit requires higher frequency than in a slow muscle for activation. The reference function 620 represents a slow muscle, where a motor unit requires lower frequency than in a fast muscle for activation. A mapping of a measure or multiple measures to the decision surface may be used to obtain a prediction of muscle state progression. By adding multiple measures to the mapping procedure, the precision and accuracy of the mapping may be increases which further enhances the quality of the prediction. Still further, the mapping may be used as an estimate of a different muscle state. According to an embodiment of the invention, the mapping may be used to indicate a progressive change in a muscle fiber type distribution, when population data as described in FIG. 5c is used for the analysis. The reference function 630 represents a muscle state with abnormal properties, such as in a demyelinating disease, where the correlation with activation frequency and incremental force differs significantly from the two other normal (healthy) muscle state progression estimates.

Figure 6D:
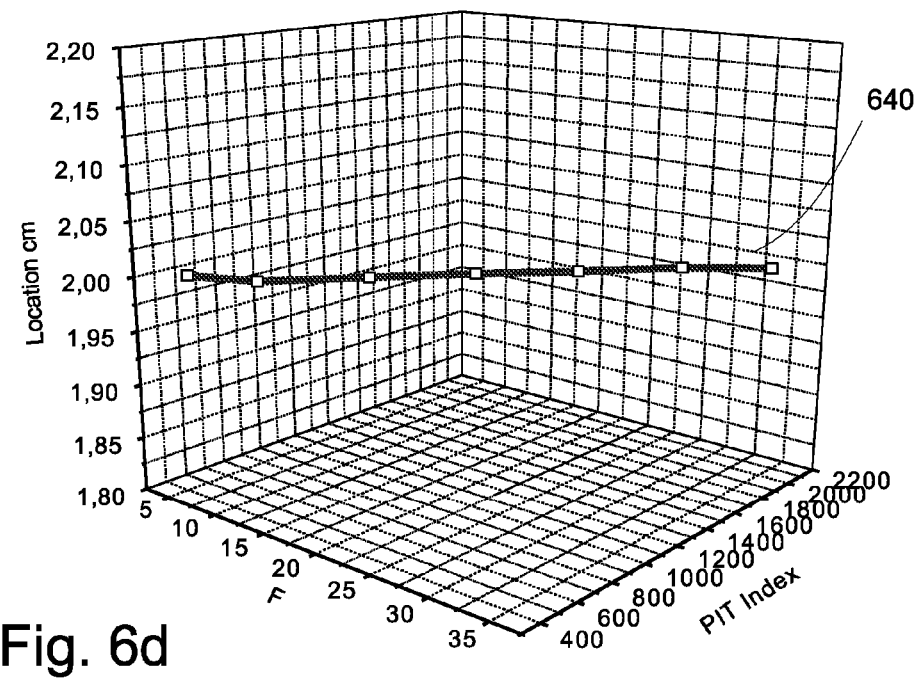
FIG. 6d shows a multi-dimensional diagram of reference function for mapping to determine prediction of muscle state progression or to determine muscle fibre subtype distribution.

FIG. 6d shows a multi-dimensional diagram with a reference function 640 for mapping to determine prediction of muscle state progression or to determine muscle fibre subtype distribution. In this diagram, the decision surface has an additional third parameter (axis) representing the location of the measure, which may be used to show the horizontal location and/or depth of the muscle. This may be used, for example, to optimize a training session or to determine problems or pains during an exercise or due to an altered muscle state. The decision surface mapping may further be used to locate neuromuscular problems, as the depth location of data signal may identify the muscle, and the horizontal (along the skin surface) information may identify the place of a neuromuscular junction. In a training exercise a person may have instantaneous information available in which to adapt his exercise load and repeats. The three parameters (axes) described in the diagram (PIT index, incremental force and location) are non-limiting examples of parameters that may be used to create a reference function, and are meant as an indication that various parameters, in addition to the said parameters, may be used to create a reference function to determine a muscle state, a prediction of muscle state progression or a muscle fibre subtype distribution.

Figure 7A:
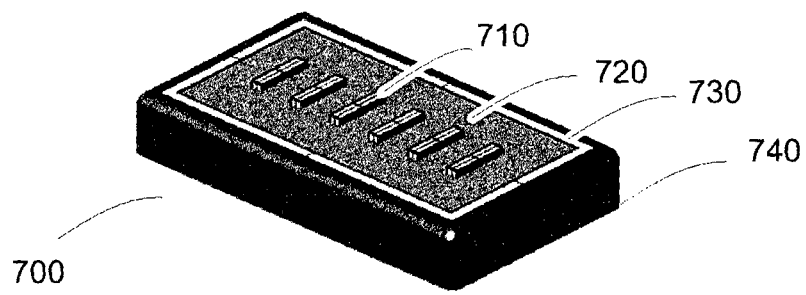
FIGS. 7a, 7b and 7c show electrode unit setups according to an embodiment of the invention.
Figure 7B:
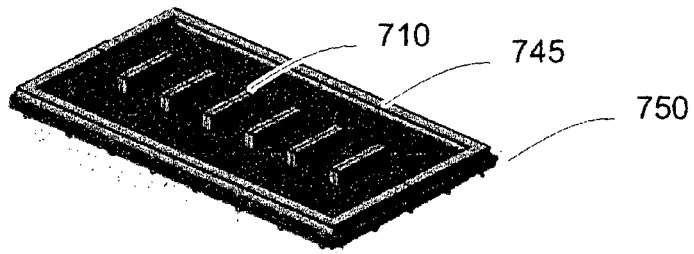
Figure 7C:
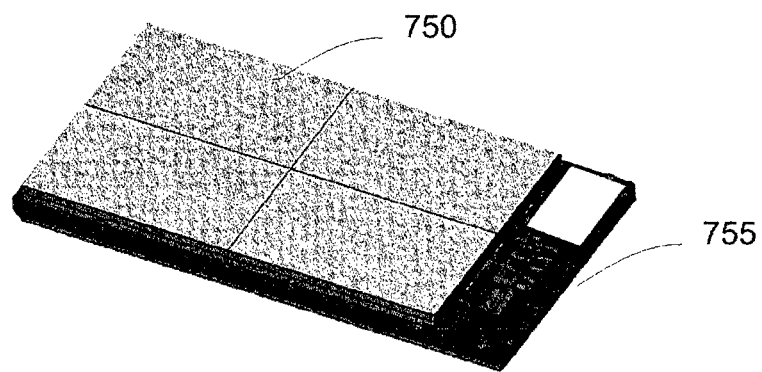

FIGS. 7a, 7b and 7c show electrode unit setups according to an embodiment of the invention. In FIG. 7a is shown an electrode unit 700, which may comprise an electrode arrangement 710, which may be surrounded by an insulator 720 and a ground element 730. The components may be located inside a casing 740, which may also act as a passive earth body. In FIG. 7b is shown the electrode arrangement 710, and a ground body 745 located on a first side of a printed circuit board 750. The ground body or ground element 745 may at least partially or completely surround the setup. The term surrounding may be understood loosely so that the ground body merely extends away from the set of electrodes, and is, for example, placed on at least two opposite sides of the electrodes. The ground body may also extend in the depth dimension so that it forms a box open from one side around the electrodes (the box may have a passage for the electrode wires). In FIG. 7c is shown a printed circuit board 755 and a passive earth body 750. The electrode arrangement 710 may be located on the first side of the printed circuit board 755, as described in FIG. 7b. The passive earth body 750 may essentially encompass electronics such as signal amplifiers and an analogue-to-digital transformer, which may be used to receive and handle signals from the electrode arrangement 710. The passive earth body 750 may also be connected to the ground body 745 depicted in FIG. 7b. In other words, the passive earth body may be arranged to make electrically conductive contact with the skin from one or more sides of the electrode arrangement. The passive earth body 750 may also extend to cover the printed circuit board 755 on top of the electrode arrangement 710, and the passive earth body 750 and the printed circuit board 755 may be arranged to comprise an opening or a recess to which the electrodes and the electronics may be installed. In other words, the passive earth body 750, which may be passive, semi-passive or, in some occasions, active, may be located on top of the printed circuit board 755 and the thus formed structure may essentially encompass electronics between the passive earth body and the printed circuit board. The meaning of the word 'encompassing' may be understood in a broad sense, and may according to an embodiment be formed by for example a casing surrounding the electronics. The said casing may further extend around the printed circuit board 755, or alternatively through the printed circuit board 755 and be connected to the ground body 745 in contact with skin surface. According to an embodiment, the passive earth body 750 may thus essentially encompass or surround the electronics, the printed circuit board 755 and the electrodes 710 and be in contact with the skin surface.

The various embodiments of the invention can be implemented with the help of computer program code that resides in a memory and causes the relevant apparatuses to carry out the invention. For example, a hand-held analysis device may comprise circuitry and electronics for acquiring, receiving and analyzing data, computer program code in a memory, and a processor that, when running the computer program code, causes the device to carry out the features of an embodiment. Yet further, a separate analysis device may comprise circuitry and electronics for handling, receiving and transmitting data, computer program code in a memory, and a processor that, when running the computer program code, causes the device to carry out the features of an embodiment. Still further, a separate acquisition unit or an analysis device with a connection to a server comprising a database may comprise circuitry and electronics for handling, receiving and transmitting data, computer program code in a memory, and a processor that, when running the computer program code, causes the device and the server comprising the database to carry out the features of an embodiment.

It is obvious that the present invention is not limited solely to the above-presented embodiments, but it can be modified within the scope of the appended claims.

The invention claimed is:

1. An apparatus for measuring a skeletal muscle signal, comprising:
   electrodes of conducting material configured to be disposed on and make contact with a skin surface when said apparatus is operated, said electrodes forming at least two pairs of electrodes for picking up the skeletal muscle signal, wherein a distance between electrodes in respective ones of said at least two pairs of electrodes is different, thereby creating a different depth sensitivity for respective pairs of the said at least two pairs of electrodes;
   an electrical insulator configured to be disposed on and make contact with the skin surface, the electrical insulator surrounding at least one of said electrodes disposed on the skin surface; and
   an earth body of a conducting material configured to be disposed on and make contact with the skin surface when said apparatus is operated, the earth body having an inner perimeter that defines an open interior area on the skin surface, said inner perimeter of the earth body surrounding said electrodes together as at least two pairs within the open interior area, the earth body configured to limit said at least two pairs of electrodes from picking up a signal along the skin surface generated from outside of an extent of said earth body;
   electronics to receive and handle signals from said at least two electrode pairs, and
   wherein said earth body encompasses said electronics to receive and handle signals from said at least two electrode pairs.

2. An apparatus according to claim 1, wherein the at least two pairs of said electrodes are arranged in either a linear setting essentially along one line or in a crossed setting, in which straight lines between electrodes in each of the at least two pairs of electrodes form a straight angle cross.

3. An electrode device for measuring skeletal muscle signals, said electrode device comprising:
   electrodes of conducting material arranged to make contact with a skin surface when said electrode device is used, said electrodes forming at least two electrode pairs for picking up the skeletal muscle signals, wherein a distance between electrodes in respective ones of said at least two pairs of electrodes is different, thereby creating a different depth sensitivity for respective pairs of the said at least two pairs of electrodes,
   an electrical insulator configured to be disposed on the skin surface and surrounding at least one of said electrodes,
   an earth body of a conducting material configured to be disposed on and make contact with the skin surface when said electrode device is used, the earth body having an inner perimeter that defines an open interior area along the skin surface, said inner perimeter of the earth body surrounding the electrical insulator and said electrodes together as at least two pairs within the open interior area, the earth body configured to limit said at least two pairs of electrodes from picking up a signal along the skin surface that is generated from outside of an extent of said earth body, and
   electronics to receive and handle the muscle signals from said at least two electrode pairs, wherein said earth body essentially encompasses said electronics.

4. An electrode device according to claim 3 comprising said at least two pairs of electrodes in total wherein said at least two pairs of electrodes are arranged in either a linear setting essentially along one line or in a crossed setting, in which straight lines between electrodes in each of the at least two pairs of electrodes form a straight angle cross.

5. An electrode arrangement for use in a skeletal muscle state analyzer, said electrode arrangement comprising:
   electrodes of conducting material configured to be applied to and make contact with a skin surface when said electrode arrangement is operated, said electrodes forming at least two pairs of electrodes for picking up a skeletal muscle signal, wherein a distance between electrodes in respective ones of said at least two pairs of electrodes is different, thereby creating a different depth sensitivity for respective pairs of the at least two pairs of electrodes,
   an electrical insulator configured to be disposed on the skin surface and surrounding at least one of said electrodes disposed on the skin surface, and
   an earth body of a conducting material configured to be disposed on and make contact with the skin surface when said electrode arrangement is operated, the earth body having an inner perimeter that defines an open interior area along the skin surface, said inner perimeter of the earth body surrounding the electrical insulator and said electrodes together as at least two pairs within the open interior area along the skin surface, the earth body configured to limit said at least two pairs of electrodes from picking up a signal along the skin surface that is generated from outside of an extent of said earth body; and
   electronics to receive and handle signals from said at least two electrode pairs, and wherein said earth body is arranged to essentially encompass said electronics.

6. An electrode arrangement according to claim 5, wherein the at least two pairs of said electrodes are arranged in either a linear setting essentially along one line or in a crossed setting, in which straight lines between electrodes in each of the at least two pairs of electrodes form a straight angle cross.

7. The electrode arrangement of claim 5, wherein an area between individual ones of the electrodes is free of the earth body.

8. The electrode arrangement of claim 5, wherein the at least two electrode pairs form a group of electrodes and an extent of the earth body surrounding the group of electrodes is limited to a perimeter region of the group of electrodes.

9. A method for analyzing skeletal muscle signals, the method comprising:
   measuring a signal from a skeletal muscle using the electrode arrangement according to claim 5,
   determining a measure indicative of frequency content of said signal,
   determining a measure indicative of strength of said signal in a high frequency, wherein said high frequency essentially corresponds to frequencies produced by the skeletal muscle in a passive involuntary tension state, and wherein said high frequency is higher in frequency than a normal frequency, wherein said normal frequency essentially corresponds to frequencies produced by the skeletal muscle in a non-tired state,
   creating a mapping using said measure indicative of strength and a reference function, said reference function being indicative of skeletal muscle states, and
   determining a skeletal muscle state based on said mapping.

10. A method according to claim 9, comprising:
    using said mapping and said reference function to determine a prediction of skeletal muscle state progression in time.

11. A method according to claim 9, comprising:
    receiving a plurality of skeletal muscle signals from at least two different skeletal muscle states, and
    determining said measure indicative of strength for said plurality of skeletal muscle signals,
    determining a skeletal muscle state estimate based on result of said mapping.

12. A method according to claim 9, wherein said reference function is based on a population database of skeletal muscle states, such that a number of individuals is measured to create said database, or an individual is measured a plurality of times to create said database.

13. A method for analyzing skeletal muscle signals, said method comprising:
    acquiring a signal from a skeletal muscle at rest from a top of said skeletal muscle using an electrode arrangement according to claim 5,
    determining a moment value of a spectrum of said signal, wherein said moment is indicative of a measure determined by multiplying a frequency value of a frequency bin with an amplitude value of the same bin to form a bin product and summing bin products for different frequencies, and wherein said moment value corresponds to frequency content of said signal,
    determining whether said moment has a normal value, a low value or a high value, corresponding to a normal, low and high frequency content of said signal, respectively,
    determining that the skeletal muscle is in a non-tired state if said moment has the normal value,
    determining that the skeletal muscle is in a tired state if said moment has the low value,
    determining that the skeletal muscle is in a passive involuntary tension state if said moment has the high value, and
    guiding an exercise using a determined state of said skeletal muscle.

* * * * *

UNITED STATES PATENT AND TRADEMARK OFFICE
CERTIFICATE OF CORRECTION

PATENT NO. : 9,844,697 B2  
APPLICATION NO. : 14/397480  
DATED : December 19, 2017  
INVENTOR(S) : Mika Herrala et al.

Page 1 of 1

It is certified that error appears in the above-identified patent and that said Letters Patent is hereby corrected as shown below:

On the Title Page

Column 1, Item (73), the country of the Assignee is Finland (FI)

Signed and Sealed this  
Fifth Day of June, 2018

Andrei Iancu  
*Director of the United States Patent and Trademark Office*